(12) United States Patent
Kriek

(10) Patent No.: US 7,297,165 B1
(45) Date of Patent: Nov. 20, 2007

(54) JOINT PROSTHESES

(75) Inventor: Hans Rudolf Kriek, Bussum (NL)

(73) Assignee: Ardemed Innovations Limited, Engomi, Nicosia (CY)

( * ) Notice: Subject to any disclaimer, the term of this patent is extended or adjusted under 35 U.S.C. 154(b) by 182 days.

(21) Appl. No.: 10/415,822

(22) PCT Filed: Nov. 2, 2000

(86) PCT No.: PCT/GB00/04201

§ 371 (c)(1),
(2), (4) Date: Jul. 31, 2003

(87) PCT Pub. No.: WO01/32109

PCT Pub. Date: May 10, 2001

(51) Int. Cl.
*A61F 2/38* (2006.01)
(52) U.S. Cl. .................... 623/20.21; 623/18.11
(58) Field of Classification Search .. 623/13.11–13.15, 623/18.11, 20.11–20.29, 20.32, 23.39
See application file for complete search history.

(56) References Cited

U.S. PATENT DOCUMENTS

| 3,765,033 | A | * | 10/1973 | Goldberg et al. | ........ 623/20.26 |
|---|---|---|---|---|---|
| 3,772,709 | A | * | 11/1973 | Swanson | ................. 623/20.12 |
| 3,969,773 | A | * | 7/1976 | Menschik | ................ 623/20.24 |
| 5,282,867 | A |   | 2/1994 | Mikhail |   |
| 5,314,481 | A | * | 5/1994 | Bianco | .................... 623/20.25 |
| 5,411,555 | A | * | 5/1995 | Nieder | .................... 623/20.26 |
| 5,755,804 | A | * | 5/1998 | Schmotzer et al. | ...... 623/20.24 |
| 5,800,552 | A | * | 9/1998 | Forte | ....................... 623/20.27 |
| 5,888,203 | A | * | 3/1999 | Goldberg | ................. 623/13.11 |
| 6,371,124 | B1 | * | 4/2002 | Whelan | ..................... 128/898 |

FOREIGN PATENT DOCUMENTS

DE 3741492 A 6/1989
GB 1349587 4/1974

* cited by examiner

*Primary Examiner*—Bruce Snow
*Assistant Examiner*—Cheryl Miller
(74) *Attorney, Agent, or Firm*—Diederiks & Whitelaw, PLC

(57) ABSTRACT

Joint prostheses are provided which may be used to replace, for example, knee, elbow or ankle joints. A knee prosthesis comprises a pin and a pivoting member. The pin bridges a gap between a medial condyle and lateral condyle of a femur. The pivoting member is positioned in the gap and the pin passes through the pivoting member to secure it in position and to allow it to pivot about the pin. The pin and pivoting member of the prosthesis represent a mechanically convenient system which is able to replace the function of a joint and can be positioned with less trauma to the joint whose function they replace than prostheses according to the prior art.

27 Claims, 8 Drawing Sheets

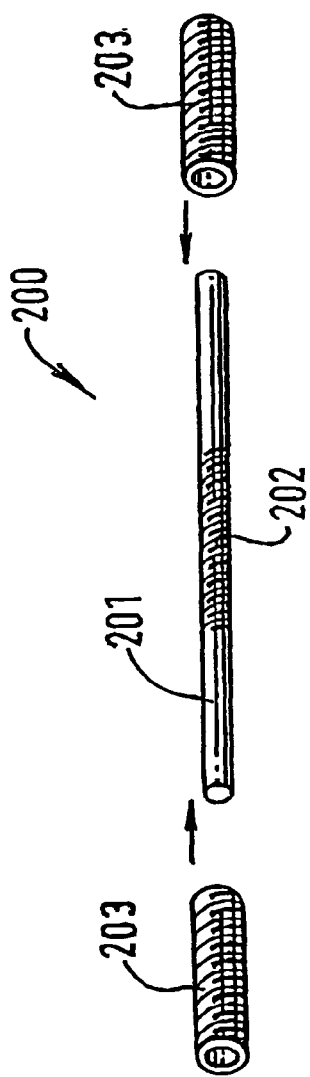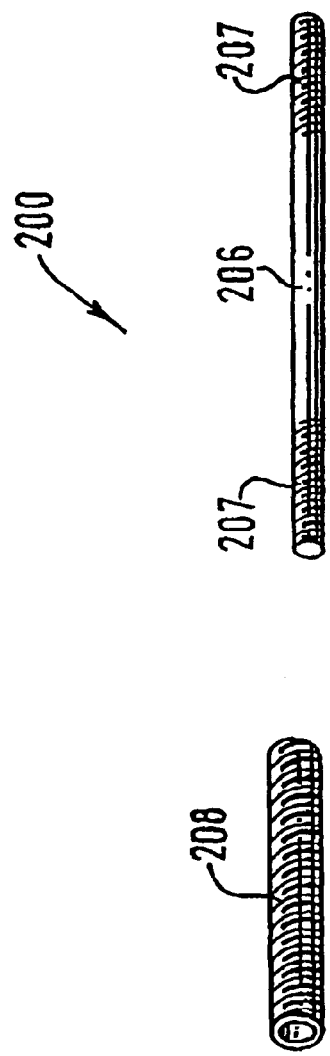

JOINT PROSTHESES

RELATED APPLICATIONS

This application is a 371 national stage entry of PCT/GB00/04201 filed Nov. 2, 2000.

BACKGROUND OF THE INVENTION

1. Field of the Invention

This invention relates to joint prostheses and to methods of placing joint prostheses in human or animal bodies.

2. Discussion of Prior Art

Replacement of worn out, damaged or diseased joints of human or animal bodies with artificial joint prostheses or components is an established medical procedure. Conventional joint prostheses or components for use in such procedures, which have been designed for virtually all types of joints, generally comprise component parts of the same or similar shape or form as all or part of the natural joint they are designed to replace. For example, the condyle surfaces of a knee joint may be replaced with metal plates of the same shape as the surfaces they replace. Alternatively, a whole joint may be replaced with a metal joint prosthesis taking a generally similar form to the original knee.

This conventional approach to joint replacement has various disadvantages. Firstly, the component parts of such joint prostheses are usually large and require invasive surgical procedures to put the prosthetic components in place. Secondly, although the artificial component parts may have the same shape as the original natural joints, they cannot provide the same function as they are made from artificial material rather than bone and/or body tissues. For example, when the condyle surface of a knee is replaced the articular cartilage is removed and the new artificial surface will not be lubricated in the same way as a natural knee. This results in wear both of the artificial components and the body tissue surrounding or coming into contact with the artificial component.

SUMMARY OF THE INVENTION

The Applicants have recognised that significant advantages can be gained by taking a new approach to the design of joint prosthesis. This involves replacing the function of a natural joint without necessarily using component parts having the same or similar shape or form as the joint whose function they replace.

Thus, according to the present invention there is provided a prosthesis for a joint comprising: a pivoting member and a pin, the pivoting member and pin being engageable with respective bones to be pivotally interconnected by the prosthesis, the pin being adapted in use to bridge a recess in a bone, or a recess defined between two bones, and to engage the pivoting member such that the pivoting member can pivot about the longitudinal axis of the pin.

Also according to the present invention there is provided a method of replacing a joint comprising: engaging a pivoting member and a pin with respective bones to be pivotally interconnected, the pin being mounted such that it bridges a recess in a bone, or a recess defined between two bones, and the pin engaging the pivoting member such that the pivoting member can pivot about the longitudinal axis of the pin.

Such a joint prosthesis may for example replace a knee joint. The recess may then be formed by reaming out somewhat the naturally occurring gap between the femoral condyles of a femur. The pivoting member may then engage a tibia, the pin may be positioned along an axis passing between the femoral condyles of the femur, and the prosthesis may provide pivoting about this axis to achieve the natural function of the joint.

In another example, the joint prosthesis may replace an elbow joint. The recess may then be formed by reaming out somewhat the naturally occurring gap between the medial and lateral condyles of a humerus. The pivoting member may then engage an ulna, the pin may be positioned along an axis passing between the condyles of the humerus and the prosthesis may provide pivoting about this axis to achieve the natural function of the joint. In yet another example, the joint prosthesis may replace an ankle joint. The recess may then be the naturally occurring gap (reamed out if necessary) between the medial malleolus and the lateral malleolus of the fibula and tibia respectively, the pivoting member may engage the talus (or the medial malleolus and the lateral malleolus), the pin may be positioned along an axis between the medial malleolus and the lateral malleolus through the talus, and the prosthesis may provide pivoting about this axis to achieve the natural function of the joint. Reaming out of the recess may be necessary to allow the talus to move freely in the recess.

The pin and pivoting member of the prosthesis represent a mechanically convenient system which is able to replace the function of a joint. Furthermore, they can be positioned with less trauma to the joint whose function they replace than prostheses according to the prior art, since the pin and pivoting member form a hinge or pivot type arrangement which is generally smaller than that of the original joint and more compact than known prosthesis. Consequently a prosthesis of the invention is capable of being fixed in place with a lesser amount of removal of bone and tissue from the area of the joint than the prior art.

Furthermore, relatively large surfaces of the bone around the joint which has been replaced may float clear of one another and bear substantially no load. This reduces any further wear of these surfaces and reduces the likelihood of the need to carry out further procedures to replace the joint again.

Preferably, the pivoting member comprises a sleeve for engaging the pin. The pin may pass through the sleeve allowing the pivoting member to rotate relative to the pin and may additionally secure the pivoting member in place. This arrangement is particularly straightforward to position in a body and positioning involves minimal trauma to the joint.

In particular, for an ankle, the pivoting member may comprise a sleeve adapted to be fitted in a bore in a talus. In use, the sleeve engages the inside surface of the bore, and the pin passes through and extends beyond the sleeve such that its end portions engage and are supported by the medial malleolus and lateral malleolus. Alternatively, the sleeve comprises two parts, one inserted in and supported by the medial malleolus and a second inserted in and supported by the lateral malleolus. The pin then passes through the sleeve parts and engages in a bore formed in the talus. Thus, in either of these embodiments the talus, fibula and tibia can rotate about the axis of the pin, replacing the natural movement of the joint.

The pivoting member, particularly when for use in a knee or an elbow, may further comprise one or more supports extending from the sleeve to a bone to be interconnected by the prosthesis. The support(s) of the pivoting member support weight exerted through the joint and rotate about the longitudinal axis of the pin allowing the bone engaged by the pivoting member to also rotate about the longitudinal axis of the pin, providing the function of the joint being replaced.

Preferably, each support has a base that engages, in use, the end of the bone to be engaged by the pivoting member. The base(s) may rest, in use, on a prepared surface of the bone. In this case the base(s) remain securely in place due to weight exerted through the joint and natural tension provided across the joint by muscles and ligaments etc. Alternatively, the base(s) may be secured to the end of the bone. This may be achieved, for example, by screwing the base(s) to the bone. Alternatively it may be achieved by cementing the base(s) to the bone.

In another embodiment, the support(s) may extend into the bone, or a bore in the bone, and a base for such a support may comprise a peg extending, in use, through the bone to be engaged by the pivoting member. In other words, the peg may extend across the bone, i.e. substantially perpendicular to the length of the bone. The peg may extend substantially from the anterior to the posterior of the bone. Alternatively, the peg may extend substantially from the lateral to the medial side of the bone. In this latter case, a single peg may be provided for more than one support. The support(s) can engage the peg(s) when mounted in the bone such that load is exerted on the bone via the peg(s). This is particularly advantageous as it allows the end (condyle) surfaces of the bone to remain largely intact.

In one embodiment particularly suitable for use in the knee, the pivoting member comprises two such supports. One for supporting the medial side of the knee joint by interconnecting, in use, the medial condyle of a femur and the medial condyle of a tibia, and the other for supporting the lateral side of the knee joint by interconnecting, in use, the lateral condyle of a femur and the lateral condyle of a tibia. The provision of a pivoting member comprising two separate supports allows the joint prosthesis to be fitted in a procedure that causes particularly little trauma to the central area of the knee joint. More specifically, the supports may be generally elongate and may be mounted via bores in the tibia or via bores in the femur, and the central portion of the knee joint can remain largely undisturbed.

In another embodiment particularly suitable for use in the knee, the pivoting member comprises one such support. The support may then be positioned centrally in the joint to allow the condyle surfaces of the femur and tibia to remain entirely, or almost entirely, intact.

As joints, even of the same type, have dimensions which vary considerably, the pivoting member may be adjustable to accommodate different distances between the pin and the bone which the pivoting member engages. To achieve this, the support(s) may have adjustable length.

Some natural joints allow a small degree of movement around axes other than the major axis of rotation of the joint. For example, a knee joint may bend to a few degrees from side to side as viewed frown the front (i.e. the anterior view). Such "bending" movement in joints may be accommodated by the pivoting member. The pivoting member may therefore further comprise means for rotating about an axis substantially perpendicular to both the major axis of the pin and the major axis of at least one of the bones to be connected by the joint. The rotation may be resilient to improve support of the joint by the prosthesis.

For example, the support(s) may resiliently extend and contract along its/their length between the pin and its/their base(s). Thus, when the pivoting member has two supports, the relative extension and contraction between two supports provides a suitable bending movement to accommodate the desired rotation. The extension and contraction may be provided by a piston and cylinder arrangement. Alternatively the bending movement may be provided by the support(s) themselves flexing. This is particularly useful when the pivoting member has only one support and flexation of the support directly accommodates desired rotation.

In an alternative embodiment, again suitable for use with a knee or elbow, the pivoting member may be provided with a threaded stud which provides for self-tapping engagement with a bone formed in the adjacent bone whereby the member may be secured to the bone. Again, this pivoting member may be resilient or otherwise adapted to provide for limited relative movement other than the principal pivoting action of the joint, if desired.

Natural joints may also have some degree of motion around an axis which is substantially parallel to a longitudinal axis of a bone whose movement the joint facilitates. For example, a knee joint rotates around an axis passing through the medial condyle of a tibia and substantially parallel to the tibia. This "twisting" motion in joints may be accommodated by the pivoting member. The pivoting member may therefore further comprise means for rotating about an axis substantially parallel to the major axis of one of the bones connected by the joint.

For example, the base(s) of the pivoting member engaging the end of the bone may be adapted to rotate in a plane in which the base(s) contact(s) the bone. So, for a knee, a base resting on a surface of a medial condyle of a tibia may be adapted to rotate in the plane of the surface such that the central axis of rotation passes through the medial condyle of the tibia and substantially parallel to the tibia. When the pivoting member also has a base resting on the lateral condyle of the tibia, this may be arranged to slide to accommodate the rotation of the other base.

Rotation or sliding of a base may be provided by fitting the base in a sleeve positioned between the base and the bone. Alternatively, a washer or two dimensional bearing may be placed between the base and the bone.

This, in itself, represents a departure from the prior art and, according to a further aspect of the present invention there is also provided a component for a joint prosthesis adapted to rotate about an axis substantially parallel with the major axis of a bone to be interconnected by the prosthesis.

The pin preferably comprises a generally cylindrical shaft which is mounted in a bore formed in the bone, the bore having portions either side of the recess into which the pin is to be mounted. The bore is preferably made from one (i.e. proximal) side of the joint. The pin may also be inserted into the bore from the one (i.e. proximal) side of the joint (i.e. one end of the bore). In particular, the pin may be inserted into position axially. Thus, only a single small incision may be made by a surgeon to enable the bore to be made and insert the pin, greatly reducing trauma to the patient. Accordingly, the pin may be adapted to be inserted into the bore from one end, e.g. by having self tapping means at a distal end or means by which it can be engaged to aid insertion at the proximal end.

More specifically the pin may be retained in the bore by an interference fit, and may therefore have a rough or knurled surface for engaging the inside surface of the bore. In a preferred embodiment the pin has external screw threaded portions for self-tapping engagement with the inside surface of the bore. Another alternative is for the pin to be tapered and/or for it to be fitted in a tapered bore. Additionally or alternatively, the pin may be cemented in position. In each case, the pin bridges a recess defined in or between bones and its ends are supported in bore portions either side of the recess.

In a particularly preferred form of the method for a knee or elbow joint, the pin is inserted into position via a bore portion extending completely through the bone on one side of the recess, which is made by the surgeon and which communicates with the recess. The sleeve is aligned with such bore portion and the pin inserted such that it passes through the sleeve and into an opposed bore portion formed in the bone on the other side of the recess.

Alternatively, the sleeve may be inserted in a bore portion first, and the pin then inserted through the bore inside the sleeve. This is particularly useful in an ankle. Another alternative, also useful in an ankle, is for the pin and sleeve to be inserted together through the bore, one inside the other, with the two ends of the pin extending beyond the ends of the sleeve for mounting to adjacent bone parts. This is a quick and simple way of fitting a prosthesis for an ankle.

In particularly preferred embodiments, the bore extends only part way through the bone on the distal side. For example, the distal portion of the bore may be in a portion of bone inward of the inside surface of the cortical bone wall distal from the side of the bone from which the bore is made. The pin, when inserted, may therefore extend only part way through the bone on the distal side. This is advantageous as it reduces trauma to the bone on distal side of the joint and, in particular, prevents damage to ligaments or the insertion points of ligaments on that side of the joint.

For a knee, it is preferable that the bore is made from the medial side of the femur as the medial collateral ligament has a wider insertion into the femur than the lateral collateral ligament. Thus, the medial collateral ligament can be parted to allow access to the femur to make the bore and insert the pin, and the lateral collateral ligament can remain untouched.

For an elbow, it is preferable that the bore is made from the lateral side of the humerus, as this reduces the risk of damage to the ulna nerve (nervous ulnaris) which runs through the medial side of the elbow joint.

For an ankle, it is preferable that the bore is made from the medial side of the ankle joint.

The bore portion on the proximal side may have a slightly bigger radius than that on the distal side of the recess, with the pin having self-tapping threaded, or interference fitting, portions, for example, of radii corresponding to the radii of the respective bore portions, so that the leading edge of the pin can pass freely through the proximal bore portion to aid insertion.

As exemplified above, with reference to the knee, elbow and ankle, the pin is located along the major axis of rotation of the joint. The bore is preferably also made along the major axis of rotation to locate the pin along that axis. In a knee, for example, the bore is preferably made, and the pin is located, along an axis which passes through the posterior femoral condyles as the movement of a natural knee is virtually entirely around such an axis.

Thus, according to the present invention there is also provided a knee prosthesis having a first component which engages in use the posterior femoral condyles of a knee joint and a second component which engages in use a tibia, the components being pivotally engaged, in use, in such a manner to allow the tibia to rotate about an axis extending between the posterior femoral condyles of the femur.

Also according to the invention there is provided a method of replacing a knee joint comprising mounting a first component in engagement with the posterior femoral condyles of a knee joint, and a second component in engagement with the tibia, the components being pivotally engaged, in use, in such a manner to allow the tibia to rotate about an axis extending between the posterior femoral condyles of the femur.

This knee prosthesis achieves the natural function of the knee joint in a surprisingly simple way, as virtually all the mechanical movement of the knee takes place around the axis. No further support of the knee joint is required as rotation around the axis replaces the function of the knee joint. The components may therefore only be pivotally engaged, with no other engagement or load bearing surfaces necessary.

More particularly, the axis is preferably between the apexes of the medial and lateral femoral epicondyles (the transepicondylar axis), or close to it. Such an axis is the optimal major axis of rotation for a knee, and the function of the knee can therefore be replaced using a prosthesis which rotates around such an axis.

Another of the examples mentioned above is the replacement of an elbow joint. The bore is made, and the pin is located, along an axis which passes through the epicondyles of a humerus. Such an axis is the optimal major axis of rotation for an elbow. The function of the elbow can therefore be replaced using a prosthesis which rotates around such an axis.

Thus, according to the present invention there is also provided an elbow prosthesis having a first component which engages in use the medial and lateral condyles of the humerus at an elbow joint and a second component which engages in use an ulna, the components being pivotally engaged in use in such a manner to allow the ulna to rotate about an axis extending between the epicondyles of the humerus.

Also according to the prevent invention there is provided a method of replacing an elbow joint comprising mounting a first component in engagement with the medial and lateral condyles of the humerus at the elbow joint and a second component in engagement with the ulna, the components being pivotally engaged in use in such a manner to allow the ulna to rotate about an axis extending between the epicondyles of the humerus.

Such an axis is the optimal axis of rotation of an elbow joint.

Yet another example mentioned above is the replacement of an ankle joint. The bore is made, and the pin is located along an axis which passes between the medial malleolus and lateral malleolus of the tibia and fibula respectively through the talus. The function of the ankle can therefore be replaced using a prosthesis which rotates around such an axis.

Thus, according to the present invention there is also provided an ankle prosthesis having a first component which engages in use the medial malleolus of a tibia and the lateral malleolus of a tibia at an ankle joint and a second component which engages in use a talus, the components being pivotally engaged in use in such a manner to allow the ankle to rotate about an axis extending between the medial malleolus and lateral malleolus through the talus.

Also according to the invention there is provided a method of replacing an ankle joint comprising mounting a first component in engagement with the medial malleolus of the tibia and the lateral malleolus of the fibula, and a second component in engagement with the talus, the components being pivotally engaged in use in such a manner to allow the ankle to rotate about an axis extending between the medial malleolus and lateral malleolus through the talus.

Such an axis is the optimal axis of rotation of an ankle joint.

BRIEF DESCRIPTION OF THE DRAWINGS

Preferred embodiments of the present invention will now be described, by way of example only, with reference to the accompanying drawings, in which:

FIGS. 9a and 9b are illustrations of ankle prostheses according to the invention.

DETAILED DESCRIPTION OF THE INVENTION

Figure 1:
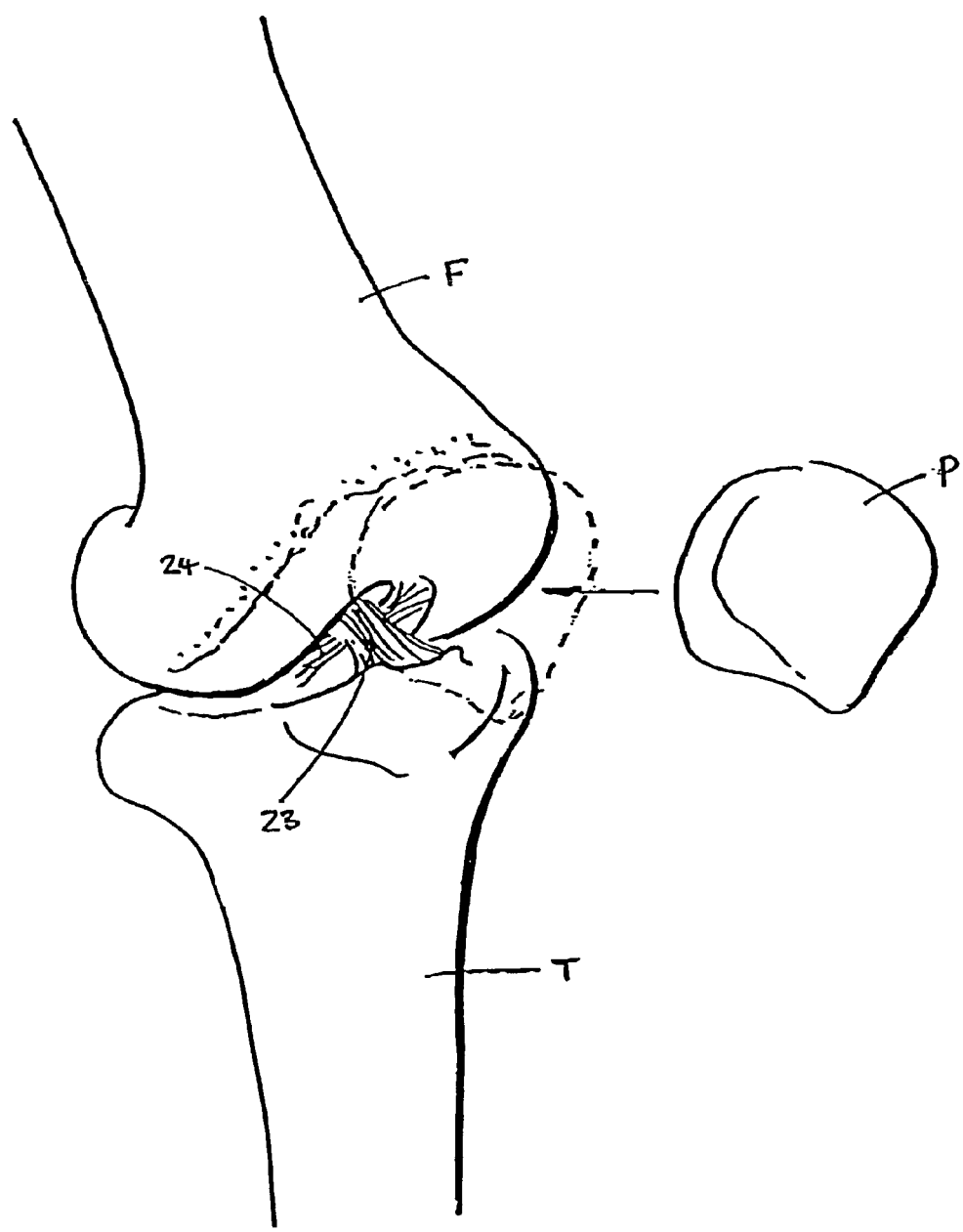
FIG. 1 is an illustration of a knee joint.
Figure 2:
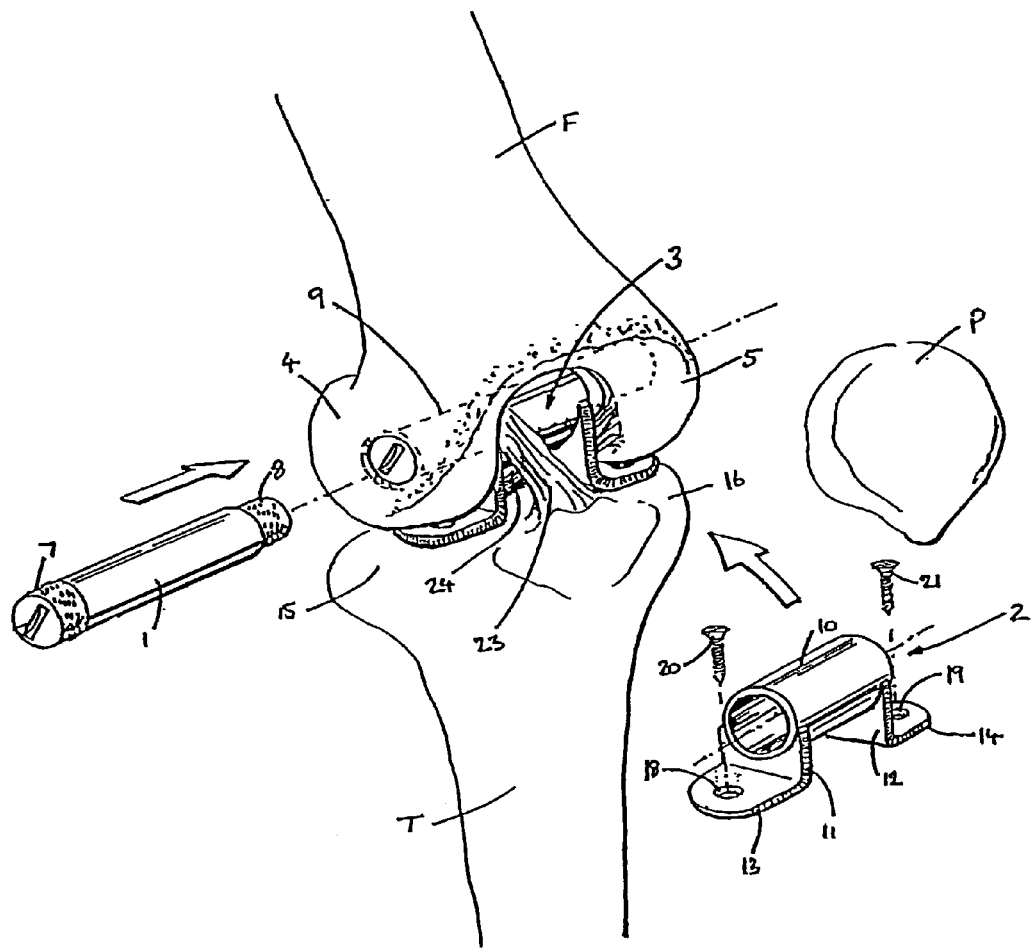
FIG. 2 is an illustration of the knee joint of FIG. 1 with a knee prosthesis according to the invention in place.

Referring to FIGS. 1 and 2, a joint prosthesis according to the invention may be applied to a knee. In this example, a knee prosthesis comprises a pin 1 and a pivoting member 2. The pin 1 bridges a gap 3 between a medial condyle 4 and lateral condyle 5 of a femur F. The pivoting member 2 is positioned in the gap 3 and the pin 1 passes through the pivoting member 2 to secure it in position and to allow it to pivot about the pin 1.

In this example, the pin 1 comprises a uniformly cylindrical bar of, for example, titanium, chrome or Polyetheretherketone (PEEK). Self-tapping threads 7 and 8 provided at the medial and lateral ends 7 and 8 of the pin 1 while the central portion of the pin 1 has a smooth surface. The pin has a diameter of, for example, 5 to 10 millimeters which allows the pin to be sufficiently strong to support the knee joint but not so large as to be too invasive on insertion into a bore 9 formed by the surgeon in the medial and lateral condyles 4 and 5 of the femur F. The threads 7 and 8 are configured to firmly engage respective portions of the inside surface of the bore 9 to secure the pin in place. The thread 8 is of slightly smaller diameter than the thread 9 and can pass freely through the portion of the bore 9 in the medial condyle 4 which is of slightly larger diameter than the portion of the bore 9 in the lateral condyle. Thus, the pin can be pushed through the medial condyle and through the pivoting member until the threads engage their cooperating bone portions after which the pin can be firmly screwed in place.

The pin 1 can alternatively be secured by a tapering fit, interference fit or by cementing.

The pin 1 has a length which allows it to extend between the medial condyle 4 and lateral condyle 5, but, in this example, the pin 1 does not extend through the outer cortical bone wall of the lateral condyle 5 proximal to the lateral collateral ligament (not shown) in order to reduce trauma to the knee joint.

The pivoting member 2 comprises a sleeve in the form of a metal tube 10 having an inner diameter suitable for fitting closely with the outer diameter of the central portion of the pin 1, and two supports 11 and 12 extending from the tube 10 to bases 13 and 14 which rest, in use, on the surface of the medial and lateral condyles 15 and 16 of a tibia T. In this example the supports 11, 12 and bases 13, 14 comprise solid component parts connected to the tube 10. The bases 13, 14 have holes 18, 19 for receiving screws 20, 21 which are screwed into the condyles 15, 16 of the tibia T.

In another example, the bases 13, 14 are cemented to the condyles 15, 16 of the tibia T.

In yet another example the bases 13, 14 are not screwed or cemented to the condyles 15, 16, but simply rest on the surface of the condyles 15, 16 or in recesses cut by the surgeon into the surfaces of the condyles 15, 16.

In order to permit a degree of rotational movement around the axis of the holes 18, 19, whether or not the bases 13 and 14 are secured to the condyles 15, 16, a washer or two-dimensional bearing can be provided between the bases and the surfaces of the condyles 15, 16. In particular rotation of the pivoting member 2 around an axis passing through the medial condyle 15 and substantially parallel to the tibia T is provided by placing a two dimensional washer between the base 13 and the surface of the medial condyle 15. In addition the base 14 is placed in a sleeve (not shown) to allow it to slide and accommodate the motion of the other base 13. The supports 11 and 12 may be provided with a certain degree of resilient movement in order to accommodate twisting and bending movements between the bases 13, 14 and the tube 10. This may be provided by a micro-piston arrangement arranged to enable the supports 11, 12 to have adjustable length in order that the pivoting member 2 can be fitted in knee joints of different sizes and dimensions.

The knee prosthesis is fitted by the surgeon first making an incision in the medial side of the knee in order that access can be gained to the gap 3 between the medial and lateral condyles 4, 5 of the femur and the condyle surfaces 15, 16 of the tibia T. The gap 3 is then reamed out to enlarge the gap 3 and provide room for receiving the pivoting member 2 and, in particular, the tube 10, although this may not be necessary.

A second incision is made in the medial side of the knee and a bore 9 is made through the lateral condyle 4, and partly through the lateral condyle 5 of the femur F. This bore 9 extends along the major axis of rotation of the knee joint, sometimes referred to as the transepicondylar axis. This axis is the axis of optimal movement of the knee joint and extends substantially between apexes of the femoral epicondyles.

As discussed above, the bore radius in the medial condyle 4 is slightly greater than the lateral condyle 5.

The surfaces of the condyles 15, 16 of the tibia T are then prepared for receiving the pivoting member 2. In this example, around 5 millimeters of bone is removed or resected from the condyle surfaces to provide room for the pivoting member 2 and in order to shape the surfaces of the condyles 15, 16 for receiving the bases 13, 14 of the supporting member 2. In another example, the surfaces of the condyles 15, 16 are not resected. In this case, if desired, the supports 11, 12 may have a length that holds the end surfaces of the femur F and tibia T apart.

The pivoting member 2 is then inserted into the space between the femur F and tibia T such that the tube 10 fits in the gap 3. The pivoting member 2 fits between the anterior and posterior cruciate ligaments 23, 24 and may be inserted without causing significant trauma or interfering with the function of these ligaments 23, 24. This has the advantage of generally reducing trauma to the knee joint and improving recovery time.

The pin 1 is then inserted from the medial side into the bore 9. The pin passes through the tube 10 and is threadedly engaged with the condyles, as discussed above, in order to secure the pivoting member 2 in place.

Figure 3:
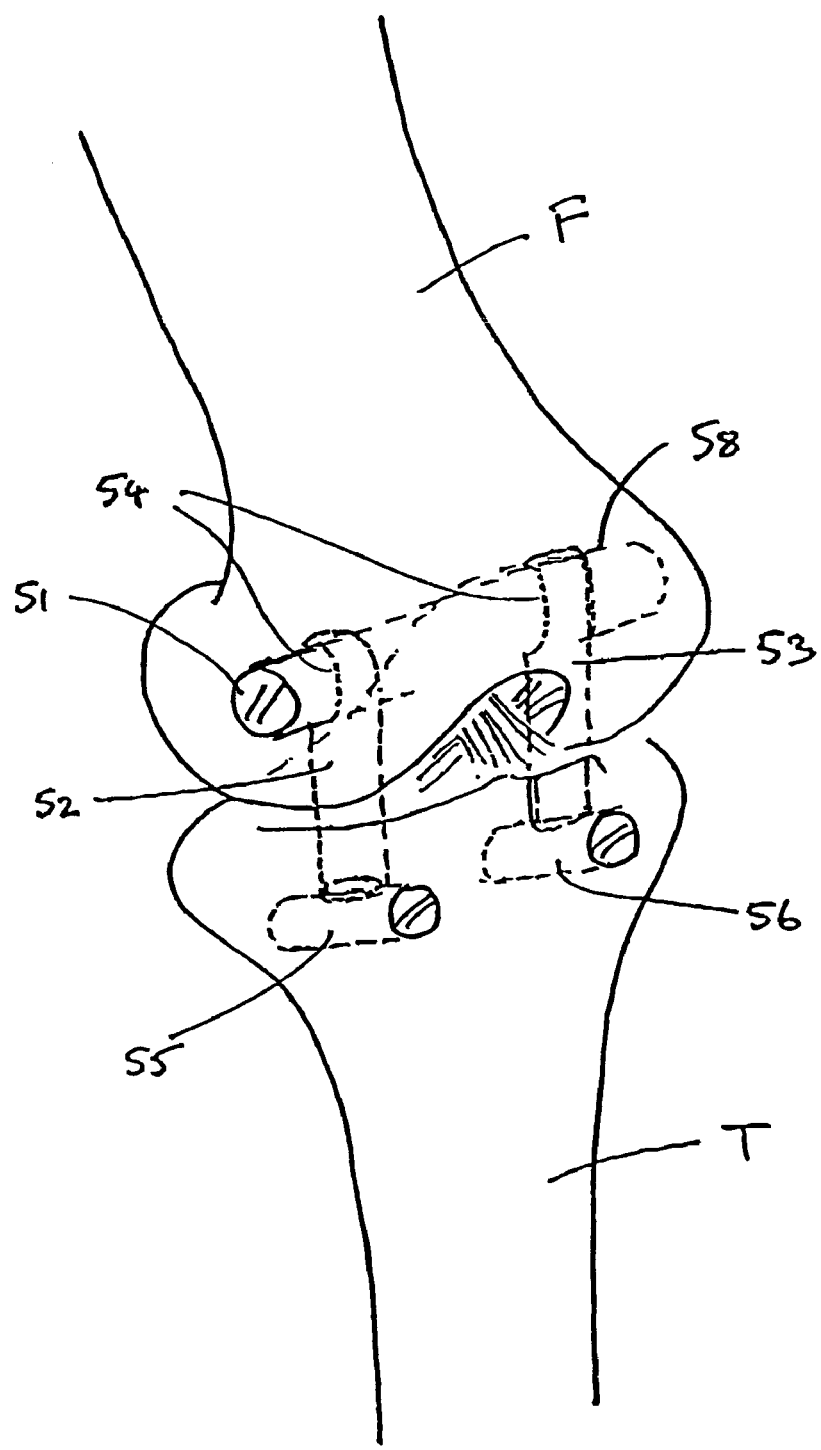
FIG. 3 is an illustration of a knee joint with a second example of a knee prosthesis according to the invention in place.

Referring to FIG. 3, a second example of a knee prosthesis comprises a pin 51 and two supports 52, 53. The pin is located in the same position as that for the first example of the knee prosthesis, and may be fitted in a similar way.

The supports 52, 53 each have an eye 54 having an inner diameter suitable for fitting closely with the outer diameter of the central portion of the pin 51 (analogous to the sleeve 10 of the first example). Each support, 52, 53 extends to a peg 55, 56. The supports 52, 53 rest on a respective peg 55, 56 such that the load exerted through the supports 52, 53 is transferred to the pegs 55, 56 and spread out in the tibia T. The pegs 55, 56 extend from the anterior to the posterior of the tibia T, although they need not extend all the way through the bone. In another example, a single peg is provided that extends from the lateral to the medial side of the tibia T.

The knee prosthesis is fitted by the surgeon making incisions to allow access to the anterior (front) of the tibia T. Peg receiving bores are then made from the anterior of the tibia T to the posterior of the tibia T for receiving the pegs 55, 56. The surgeon also makes an incision in the medial side of the knee and a bore 58 is made through the condyles of the femur F in the manner described with reference to the first example.

Further bores are made to accommodate the supports 52, 53 in the tibia T and femur F. These further bores extend from the peg receiving bores in the tibia T to the bore 58 in the femur F. In one example these further bores are made via the bore 58. In other examples these bores are additionally or alternatively made via the peg receiving bores or via a further incision in the tissue around the knee joint. The part of these bores for receiving the supports 52, 53 that is in the femur F must be large enough to allow the supports, and therefore the tibia T, to rotate around the pin 51 and provide natural movement of the knee joint.

The supports 52, 53 are then inserted in their respective bores. The eyes 54 are manoeuvred to be aligned with the bore 58 and the pin 51 is inserted in the manner described in the above example. The pegs 55, 56 are then inserted in the peg receiving bores of the tibia to engage with the supports 52, 53.

In another example, a single central support extends between the pin 51 and a peg in the tibia T. This allows a greater portion of the cartilage on the condyle surfaces of the tibia T and femur F to remain intact, and some load to remain supported by these surfaces.

Figure 4:
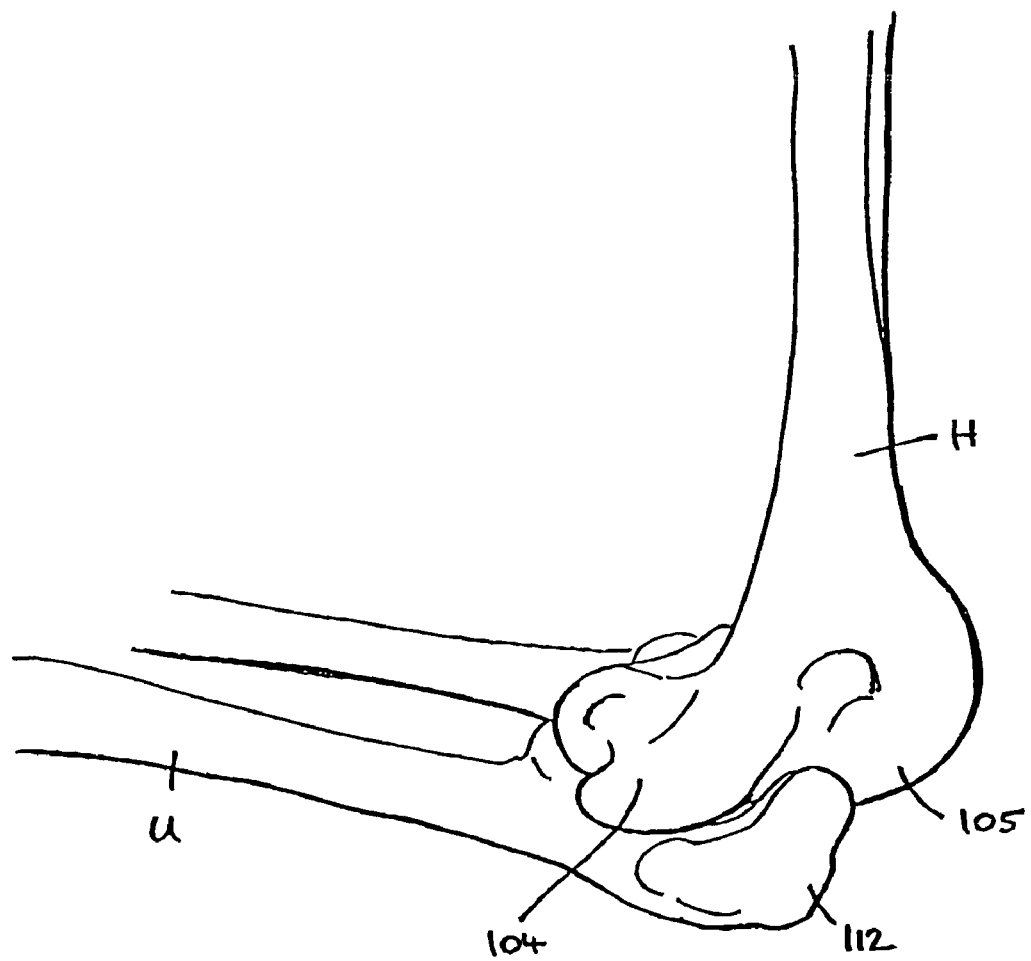
FIG. 4 is an illustration of an elbow joint.
Figure 5:
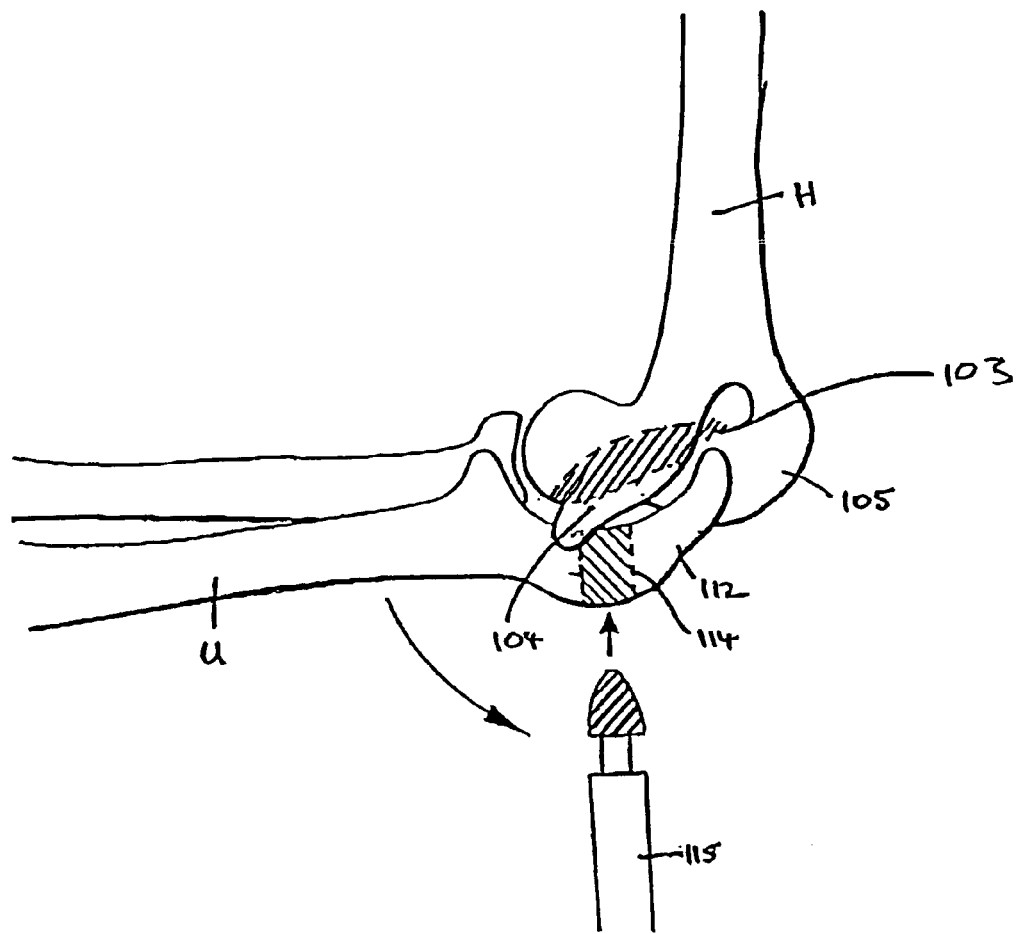
FIG. 5 is an illustration of the elbow joint of FIG. 4 during preparation for placement of an elbow prosthesis according to the invention.
Figure 6:
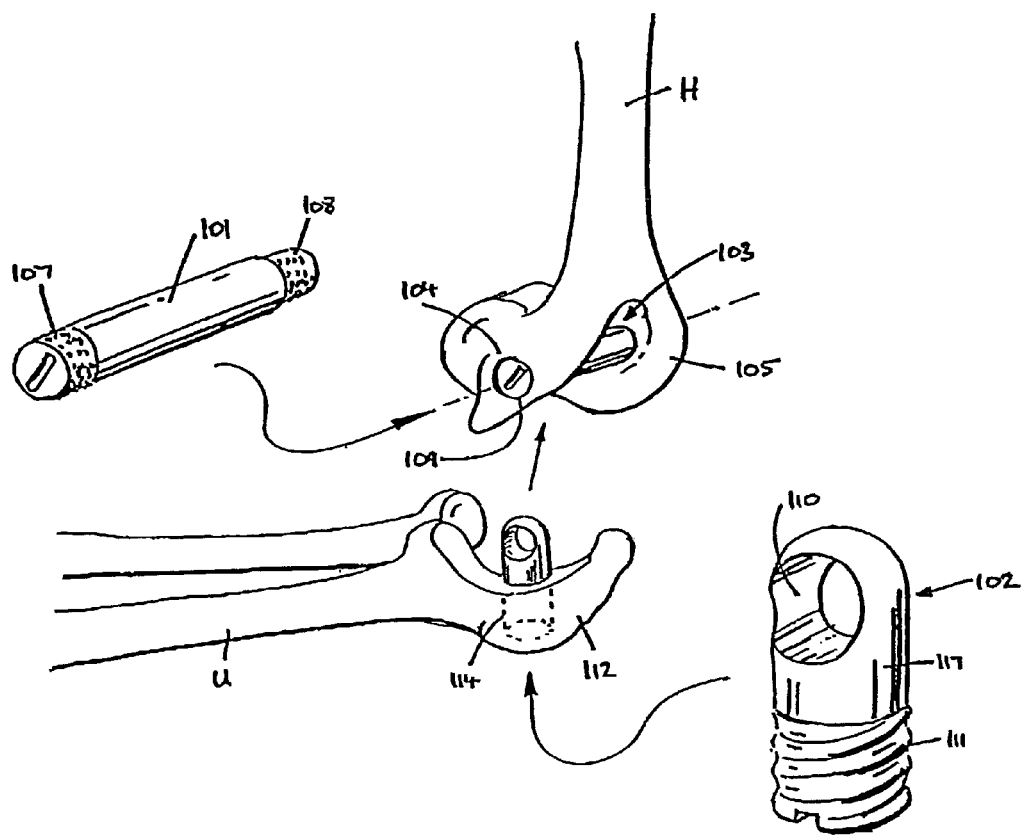
FIG. 6 is an exploded view of the elbow joint of FIG. 5 with the elbow prosthesis in place.
Figure 8:
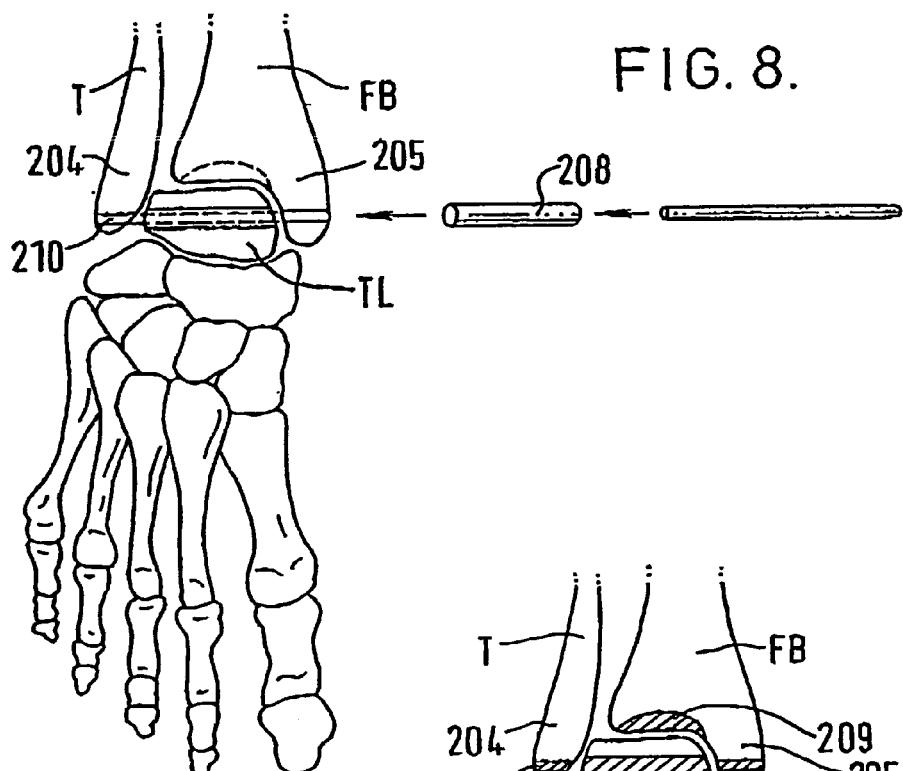
FIG. 8 is an exploded view of the ankle joint of FIG. 7 with the ankle prosthesis in place.
Figure 7:
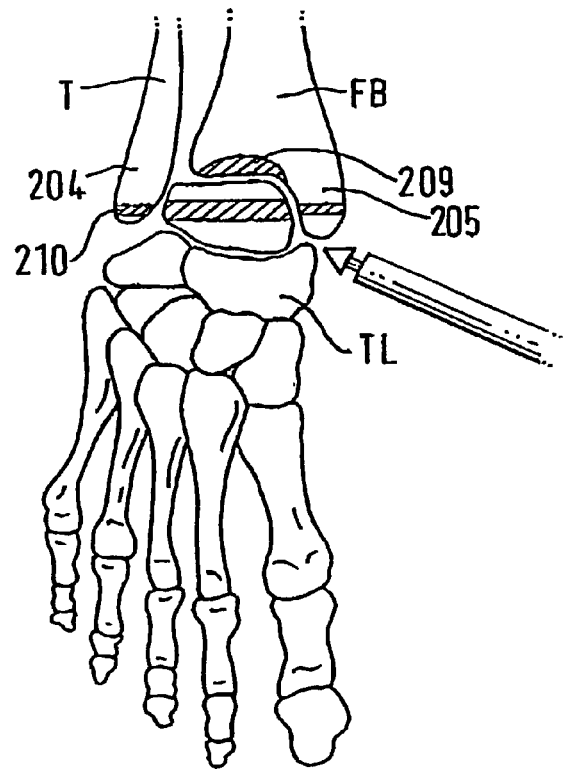
FIG. 7 is an illustration of an ankle joint during preparation for placement of an ankle prosthesis according to the invention.

Referring to FIGS. 4, 5, 6 an elbow joint can also be replaced using an elbow prosthesis. The elbow prosthesis comprises a pin 101 and a pivoting member 102. The pin 101 extends across a gap 103 between a medial condyle 104 and a lateral condyle 105 of a humerus H.

Similarly to the above, the pin 101 has self-tapping threads of surfaces 107, 108 at either end for engaging respective portions of the inside surface of a bore 109 in the medial and lateral condyles 104, 105.

The pivoting member 2 comprises an eye screw arrangement having an eye 110 (corresponding to the sleeve or tube 10 of the knee prosthesis) for engaging the pin 101 such that the pivoting member 102 can rotate around the pin 101, a body 117 and a self-tapping screw thread 111 for engaging the olecranon process 112 of an ulna U. In this example, the body 117 is metal, such as titanium or chrome. In another example (not shown) the body is arranged to resiliently flex, extend and contract to accommodate slight movement of the elbow joint other than around the axis of the pin 101.

The elbow prosthesis is fitted by first making an incision to gain access to the olecranon process 112 of the ulna U. A bore 114 is then made in the olecranon process 112 using a reaming instrument 115 as shown in FIG. 4. The gap 103 may then be enlarged (as is shown shaded in FIG. 3) using the same reaming instrument 115 through the bore 114 by manipulating the ulna U with respect to the humerus H.

A second incision is then made to gain access to the medial epicondyle of the humerus H, and the bore 109 is made through the medial and lateral epicondyles 104, 105. In a preferred example (not shown), the second incision to gain access to the lateral condyle 105 of the humerus H and the bore 109 is made through the lateral epicondyle 105 and medial condyle 104 from the lateral side of the elbow joint. In both these examples, the bore 109 need not extend all the way through the epicondyles 104, 105. Rather, the bore may only extend part way the epicondyle 104, 105, on the side remote from where the bore 109 is made. If the bore 109 is made from the medial side, the outer surface of the lateral condyle 105 can remain intact and radial collateral ligament (not shown) is not damaged. If the bore 109 is made from the lateral side, as is preferred, the outer portion of the medial condyle 104 can remain intact, avoiding the risk of damaging the nerve that runs therethrough.

After the reaming and boring procedures are completed, the pivoting member 102 is threadedly engaged with its respective bore 114 and tightened until the eye 110 extends parallel to the intended pivot axis of the joint.

The pivoting member 102 can then be located in the enlarged gap 103 with the eye 110 aligned with the bore 109, and the pin 101 is inserted in the bore 109 such that it passes through the eye 110. The pin 101 is then screwed firmly in place to anchor the prostheses in the humerus H, as is described above.

Referring to FIGS. 7, 8, 9a and 9b, an ankle joint can also be replaced using an ankle prosthesis 200. Two examples of an ankle prosthesis 200 are shown in FIGS. 9a and 9b respectively. The example in FIG. 9a comprises a pin 201 having a self-tapping threaded surface 202 at a central portion. A sleeve 203 comprises two externally threaded parts which fit slidingly over each end of the pin 201. The pin 201 has a length that allows it to extend between the lateral malleolus 204 of a tibia T to the medial malleolus 205 of a fibula FB through talus TL. The sleeve parts have dimensions suitable for fitting in the lateral malleolus 204 and medial malleolus 205 respectively.

Referring to FIG. 9b, in a second example of the ankle prosthesis 200, a pin 206 has dimensions similar to the pin 201 of the first example. However, threaded surfaces 207 are provided at either end of the pin 206 and an externally threaded sleeve 208 is arranged to fit slidingly over the unthreaded central portion of the pin 206.

The ankle joint is prepared for mounting of the ankle prosthesis 200 by a bore 210, having portions of appropriate diameter to engage respective threaded parts of the prosthesis 200, being made through the lateral malleolus 204, talus TL and medial malleolus 205. A portion of bone 209 is removed from the fibula FB to allow the talus to move freely without contact with the end of the fibula FB.

The sleeve 208 (or respective of the sleeve parts 203) is then inserted in the bore 210 and threadedly engaged with a respective portion thereof. The pin 206 or (201) is then inserted in the bore and through the sleeve 208 (or 203). In the example shown in FIG. 9a, the sleeve parts 203 threadedly engage the surface of the bore 210 in the lateral malleolus 204 and medial malleolus 205 and the threaded surface 202 of the pin 201 engages the surface of the bore 210 in the talus TL. However, the pin 201 is free to rotate in the sleeve part 203 and the talus TL can therefore rotate with respect to the tibia T and fibula FB around the longitudinal axis of the pin 201.

In the example shown in FIG. 8b, the surface of the sleeve 208 threadedly engages the bore in the talus TL, and the surfaces 207 of the pin 206 threadedly engage the lateral malleolus 204 and medial malleolus 205. Similarly, the pin 206 is free to rotate in the sleeve 208 allowing the talus TL to rotate with the tibia T and fibula FB around the longitudinal axis of the pin 206.

It will be appreciated that the respective portions of the bore 210 will be of differing relative radii, depending on which embodiment of prosthesis is used.

The invention claimed is:

1. A prosthesis for a knee joint comprising:
   a pivoting member including at least one base connected to a generally tubular sleeve, wherein the at least one base is configured to be directly mounted at a condyle portion of a tibia in a manner which maintains the sleeve in a raised position; and
   a pin having a longitudinal axis, wherein the pin is adapted to extend through a first bore portion provided in a first condyle portion of a femur, the sleeve and a second bore portion provided in a second condyle portion of a femur in order to pivotally interconnect the pivoting member and the pin in order to establish a joint of the prosthesis, wherein the pin and pivoting member are sized and configured to provide load bearing surfaces, and wherein the prosthesis is sized and configured so that, in use, the pin bridges and engages the pivoting member such that the pivoting member can pivot relative to the pin about the longitudinal axis of the pin while a clearance is maintained between condyle portions of the femur and condyle portions of the tibia.

2. The prosthesis of claim 1, wherein the at least one base, in combination with the raised position of the sleeve, is adapted to accommodate ligaments between the femur and tibia.

3. The prosthesis of claim 1, wherein the pin secures the pivoting member in place.

4. The prosthesis of claim 1, wherein the pivoting member further comprises means for rotating about an axis substantially perpendicular to both the major axis of the pin and the major axis of at least one of the bones to be connected by the joint.

5. The prosthesis of claim 1, wherein the pivoting member further comprises means for rotating about an axis substantially parallel to the major axis of one of the bones to be connected by the joint.

6. The prosthesis claim 1, wherein the at least one base of the pivoting member comprises first and second spaced bases adapted to extend from the sleeve to a bone to be interconnected by the prosthesis.

7. The prosthesis of claim 6, wherein each of said first and second bases is adapted to be directly fixed to, in use, the end of the bone from which the pivoting member is adapted to extend.

8. The prosthesis of claim 7, wherein each of the first and second bases is adapted to rest, in use, on a prepared surface of the bone.

9. The prosthesis of claim 7, wherein each of the first and second bases is adapted to be secured to the end of the bone.

10. The prosthesis of claim 1, wherein the at least one base is adapted to be secured to the tibia by a screw.

11. The prosthesis of claim 1, wherein the at least one base is adapted to be secured to the tibia by cement.

12. The prosthesis of claim 1, wherein the pin has threaded first and second spaced portions adapted to grip the femur, with the first and second spaced portions having different diameters.

13. The prosthesis of claim 1, wherein the at least one base is capable of rotating in a plane in which the at least one base contacts the tibia.

14. The prosthesis of claim 13, wherein rotation of the at least one base is provided by fitting the at least one base in a sleeve member, wherein the sleeve member is adapted to be positioned between the at least one base and the tibia.

15. The prosthesis of claim 13, wherein rotation of the at least one base is provided by a washer or two dimensional bearing adapted to be positioned between the at least one base and the tibia.

16. The prosthesis of claim 1, wherein the pin comprises a generally cylindrical shaft which is adapted to be mounted in a bore formed in the femur.

17. The prosthesis of claim 16, wherein the pin has a rough or knurled surface for engaging the inside surface of the bore.

18. The prosthesis of claim 16, wherein the pin has external screw threaded portions adapted for self-tapping engagement with the inside surface of the bore.

19. The prosthesis of claim 1, wherein the pin is adapted to be inserted axially from one side of the joint.

20. A method of replacing a knee joint comprising:
    directly mounting a pivoting member, having at least one base connected to a generally tubular sleeve, to a tibia with the at least one base being directly attached at a condyle portion of the tibia and the sleeve being vertically spaced from the tibia; and
    positioning a pin, having a longitudinal axis, in a bore having a first bore portion extending through a first condyle and a second bore portion extending into a second condyle of a femur, with the pin extending through the first bore portion, then through the sleeve and then into the second bore portion, thereby interconnecting the pin and pivoting member to establish load bearing surfaces for the joint such that the pivoting member can pivot relative to the pin about the longitudinal axis of the pin with condyle portions of the femur being maintained vertically spaced from condyle portions of the tibia.

21. The method of claim 20, wherein the pin is inserted into position axially from one side of the joint.

22. The method of claim 20, wherein the pin is inserted into position via a bore comprising a first bore portion extending completely through the femur on one side of the recess, which is made by a surgeon and which communicates with the recess.

23. The method of claim 22, wherein the bore further comprises an opposed bore portion formed in the femur on the other side of the recess, the pivoting member comprises a sleeve which is aligned with the first bore portion, with the pin being inserted to pass through the sleeve and into the opposed bore portion.

24. The method of claim 23, wherein the first bore portion on one side of the recess has a slightly bigger radius than the opposed bore portion on the other side of the recess.

25. The method of claim 22, wherein the bore is made from one side of the joint and extends only part way through the femur on a distal side.

26. The method of claim 22, wherein the bore is made from a medial side of the femur.

27. The method of claim 20, wherein a bore is made along the major axis of rotation of the joint such that the pin is located along that axis.

* * * * *